US008357350B2

(12) United States Patent
Hehir et al.

(10) Patent No.: US 8,357,350 B2
(45) Date of Patent: Jan. 22, 2013

(54) ANNULUS FIBROSUS DETECTION IN INTERVERTEBRAL DISCS USING MOLECULAR IMAGING AGENTS

(75) Inventors: Cristina Abucay Tan Hehir, Niskayuna, NY (US); Tiberiu Mircea Siclovan, Rexford, NY (US); Kenneth Michael Fish, Clifton Park, NY (US); Nicole Evelyn Barnhardt, Clifton Park, NY (US); John V. Frangioni, Wayland, MA (US); Carrie S. Vooght, Lowell, MA (US)

(73) Assignee: General Electric Company, Niskayuna, NY (US)

( * ) Notice: Subject to any disclaimer, the term of this patent is extended or adjusted under 35 U.S.C. 154(b) by 824 days.

(21) Appl. No.: 12/370,207

(22) Filed: Feb. 12, 2009

(65) Prior Publication Data

US 2010/0202965 A1    Aug. 12, 2010

(51) Int. Cl.
*A61K 51/00* (2006.01)
*A61M 36/14* (2006.01)
(52) U.S. Cl. .......... 424/1.81; 424/1.11; 424/1.65; 424/1.85; 424/1.89; 424/9.6; 534/14; 546/329
(58) Field of Classification Search .......... 424/1.81
See application file for complete search history.

(56) References Cited

U.S. PATENT DOCUMENTS

| 2003/0018136 | A1  |   | 1/2003 | Poncelet |         |
|--------------|-----|---|--------|----------|---------|
| 2005/0023442 | A1  |   | 2/2005 | Xia      |         |
| 2006/0027455 | A1  | * | 2/2006 | Patton et al. | 204/450 |
| 2006/0073541 | A1  | * | 4/2006 | Kilgore  | 435/40.5 |
| 2008/0008988 | A1  | * | 1/2008 | McKay et al. | 435/4 |

FOREIGN PATENT DOCUMENTS

| WO | WO2006007412 | 1/2006 |
|----|--------------|--------|
| WO | WO2006012309 | 2/2006 |

OTHER PUBLICATIONS

Hoffman et al. Eur. J. Med. 2009, 26, 913-935.*
Urban et al. Arthritis Research and Therapy 2003, 5, 120-130.*
Hamann et al. Experimental Neurol, 2003, 182, 300-309.*
Aoki et al., "Distribution and Immunocytochemical Characterization of Dorsal Root Ganglion Neurons Innervating the Lumbar Intervertebral Disc in Rats": A Review. Life Science 2004. 74:2627-2642.
Rajasekaran et al., "Pharmacological Enhancement of Disc Diffusion and Differentiation of healty, Ageing and Degenerated Discs: Results from In-vivo Serial Post-contrast MRI Studies in 365 Human Lumbar Discs", Eur. Spine, J. 2008; 17:626-643.
Urban et al., "Pathophysiology of the Intervertebral Disc and the Challenges for MRI", J. Magnetic Res. Imaging, 2007, 25: 419-432.
Bhushan et al., "Synthesis of Conjugatable Bisphosphonates for Molecular Imaging of Large Animals", Angew Chem. Int. Ed. Eng., 2007, 46: 7969-7971.
Degrand et al., "An Operational Near-Infrared Fluorescence Imaging System Prototype for Large Animal Surgery", Technol. Cancer Research Treat., 2003, 2:553-562.
Giroux et al., "Improved Optical Sub-system for Intraoperative near-infrared Fluorescence Imaging", Proceedings of SPIE, 2005,: 6009:60090C-60091-66009C-60010.
Tanaka et al, Imaging-Guided Oncologic Surgery Using Invisible Light: Completed Pre-Clinical Development for Sentinel Lymph Node Mapping:, Ann. Surgical Oncology, 2006; 13-1671-1681.
Fragioni, "In Vivo Near-Infrared Fluorescence Imaging", Curr. Opin. Chem. Giology, 2003; 7:626-6342003, 7:626-634.
Grinvald et al., "Improved Fluorescent Probes for the Measurement of Rapid Changes in Membrane Potential", Biophysics Journal., 1982, 39:301-308.
Grinvald et al., "Optical Recording of Sybnaptic Potentials from Processes of Single Neurons Using Intracellular Potentiometric Dyes", Biophysics Journal, 1987, 51:643-645.
Konig et al., "Vinylene Homologs of P-dimethylaminobenzaldehyde", Berichte der Deutschen Chemischen Gesellschaft, Abteilung B: Abhandlungen 1928; 61B-2074-2080.
Betz et al. "Activity-dependent Fluorescent Staining and Destaining of Living Vertebrate Motor Nerve Terminals", J. Neuroscience, 1992, 12:363-375.
Guatimosim et al., "Use of Fluorescent Probes to Follow Membrane Traffic in Nerve Terminals", Brazilian Journal of Medical and Biological Research, 1998, 31: 1491-1500.
Haughton, "Medical Imaging of Intervertebral Disc Degeneration", SPINE, vol. 29. No. 23, pp. 2751-2756, 2004.
Meyers et al., "Lighting up the Senses: FM1-43 Loading of Sensory Cells Through Nonselective Ion Channels", J. of Neurpscience, May 15, 2003, 23(10): 4054-4065.
Meyers et al., "Lighting up the Senses: FM1-43 Loading of Sensory Cells Through Nonselective Ion Channels", J. of Neurosciencxe, May 15, 2003, 23(10): 4054-4065.
Kay, Alan R., " Imaging FM Dyes in Brain Slices", Chapter 62 in "Imaging in Nuroscience and Development", 2005, Cold Spring Harbor Lab Press, Cold Spring Harbor, NY.

* cited by examiner

*Primary Examiner* — Michael G Hartley
*Assistant Examiner* — Sean R Donohue
(74) *Attorney, Agent, or Firm* — Eileen B. Gallagher

(57) ABSTRACT

The present invention relates to methods for imaging annulus fibrosus tissue and a quantitative measurement of its local concentration in a sample using an agent comprising the compound of Formula I, a $^{13}C$ or $^{2}H$ enriched compound of Formula I, an $^{19}F$-labeled derivative of Formula I, a metal-DOTA (1,4,7,10-tetra-azacyclododecane-N,N',N'',N'''-tetraacetic acid) complex of Formula I, or a radioisotope derivative of Formula I.

32 Claims, 6 Drawing Sheets

ANNULUS FIBROSUS DETECTION IN INTERVERTEBRAL DISCS USING MOLECULAR IMAGING AGENTS

BACKGROUND

Low back pain is a common health problem in industrialized societies. Studies suggest that low back pain originates from a number of spinal structures; however, the most common sources of pain are musculoligamentous injuries and age-related intervertebral disc degeneration. The intervertebral disc structure consists of the nucleus pulposus, annulus fibrosus and cartilaginous end-planes, the composition of which changes significantly with age, creating difficulty in differentiating structural changes related to age versus those associated with degeneration and back pain.

Disc structure can be accurately visualized with both computed tomography (CT) and magnetic resonance imaging (MRI); however, the correlation between disc morphology and back pain origin is poor. Current imaging methods are fundamentally limited due to their morphological assessment of functional changes that occur months to years earlier as well as lack of contrast agents specific for the disc tissues. Low back pain associated with disc degeneration is thought to be due to increased innervation of the annulus fibrosus. When a tear in the annulus fibrosus exists, the tear can be visualized using regional contrast enhancement with CT or MRI Non-surgical treatments for low back pain are often unsuccessful, and non-responding patients are typically treated with surgical intervention. There are two main surgical techniques used to treat low back pain: lumbar fusion and more recently, total disc replacement. Both techniques rely on image guidance and clear visualization of the nucleus pulposus and annulus fibrosus although presently, specific intraoperative imaging of these structures is not performed.

Therefore a contrast agent specific for the intervertebral disc could assist in the detection, diagnosis, and surgical treatment of low back pain.

BRIEF DESCRIPTION

Provided herein are methods for the qualitative or quantitative detection of annulus fibrosus of intervertebral discs in an in vitro or in vivo sample using an agent comprising the compound of Formula I,

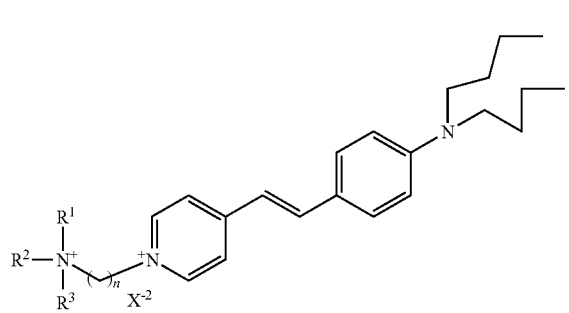

I a 13C or 2H enriched compound of Formula I, an 19F-labeled-derivative of Formula I, a metal-DOTA (1,4,7,10-tetra-azacyclododecane-N,N',N'',N'''-tetraacetic acid) complex of Formula I, or a radioisotope derivative of Formula I wherein $R^1$, $R^2$, and $R^3$ are each independently hydrogen, alkyl, substituted alkyl, fluroroalkyl, or perfluoroalkyl, n is an integer from two to four, and X is a counter ion forming a salt.

In one embodiment, the methods of diagnosing normal and pathological conditions of intervertebral discs may comprise identifying a subject at risk of, or diagnosed with low back pain: administering to the subject an agent comprising the compound of Formula I, a $^{13}$C or $^2$H enriched compound of Formula I, an $^{19}$F-labeled-derivative of Formula I, a metal-DOTA (1,4,7,10-tetra-azacyclododecane-N,N',N'',N'''-tetraacetic acid) complex of Formula I, or a radioisotope derivative of Formula I, and detecting the agent, present in the annulus fibrosus of the intervertebral disc of the subject, to enable visualization of disc structure in the subject.

In another embodiment of the method, the annulus fibrosus tissue is imaged in a surgical field of mammalian tissue comprising the steps of contacting the surgical site with an agent comprising the compound of Formula I, a $^{13}$C or $^2$H enriched compound of Formula I, an $^{19}$F-labeled-derivative of Formula I, a metal-DOTA (1,4,7,10-tetra-azacyclododecane-N, N',N'',N'''-tetraacetic acid) complex of Formula I, or a radioisotope derivative of Formula I.

In yet another embodiment, the method comprises imaging intervertebral disc structure by administering an agent comprising the comprising the compound of Formula I, a $^{13}$C or $^2$H enriched compound of Formula I, an $^{19}$F-labeled-derivative of Formula I, a metal-DOTA (1,4,7,10-tetra-azacyclododecane-N,N',N'',N'''-tetraacetic acid) complex of Formula I, or a radioisotope derivative of Formula I, and detecting the agent within the annulus fibrosus of intervertebral discs.

In still another embodiment, the methods of annulus fibrosus detection comprise contacting a tissue sample from a mammalian subject with an agent comprising the compound of Formula I, a $^{13}$C or $^2$H enriched compound of Formula I, an $^{19}$F-labeled-derivative of Formula I, a metal-DOTA (1,4,7, 10-tetra-azacyclododecane-N,N',N'',N'''-tetraacetic acid) complex of Formula I, or a radioisotope derivative of Formula I; detecting annulus fibrosus in the tissue sample by detecting the agent; and optionally quantifying the amount of the agent present in the tissue sample.

BRIEF DESCRIPTION OF THE FIGURES

These and other features, aspects, and advantages of the present invention will become better understood when the following detailed description is read with reference to the accompanying figures wherein.

DETAILED DESCRIPTION

Figure 1A:
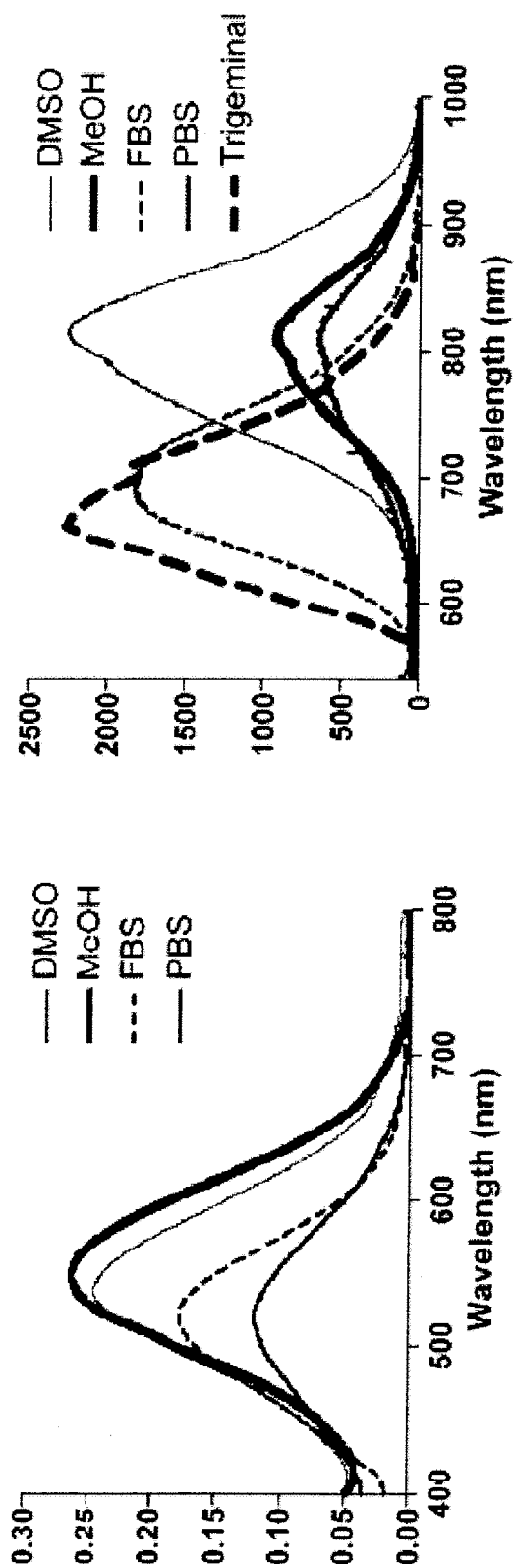
FIG. 1 shows absorbance spectra, fluorescence spectra, and summary of optical properties for in vitro and in vivo spectral properties of Formula II and IA (A and B respectfully).

The following detailed description is exemplary and not intended to limit the invention of the application and uses of the invention. Furthermore, there is no intention to be limited by any theory presented in the preceding background of the invention or descriptions of the drawings.

Definitions

To more clearly and concisely describe and point out the subject matter of the claimed invention, the following definitions are provided for specific terms, which are used in the following description and the appended claims.

"Annulus fibrosus" refers to several layers of fibrocartilage, which lie between adjacent vertebrae in the spine. Along with the nucleus pulposus, the annulus fibrosus forms the intervertebral disc. The annulus fibrosus is a strong radial tire-like structure made up of lamellae; concentric sheets of collagen fibers connected to the vertebral end plates. The sheets are orientated at various angles. The annulus fibrosus encloses the nucleus pulposus.

"Alkyl" is intended to include linear, branched, or cyclic hydrocarbon structures and combinations thereof, including lower alkyl and higher alkyl. Alkyl groups are those of C20 or below. "Lower alkyl" refers to alkyl groups of from 1 to 6 carbon atoms, preferably from 1 to 4 carbon atoms, and includes methyl, ethyl, n-propyl, isopropyl, and n-, s- and t-butyl. Higher alkyl refers to alkyl groups having seven or more carbon atoms, preferably 7-20 carbon atoms, and includes n-, s- and t-heptyl, octyl, and dodecyl. Cycloalkyl is a subset of alkyl and includes cyclic hydrocarbon groups of from 3 to 8 carbon atoms. Examples of cycloalkyl groups include cyclopropyl, cyclobutyl, cyclopentyl, and norbornyl. Alkenyl and alkynyl refer to alkyl groups wherein two or more hydrogen atoms are replaced by a double or triple bond, respectively.

"Substituted" refers to residues, including, but not limited to, alkyl, alkylaryl, aryl, arylalkyl, and heteroaryl, wherein up to three H atoms of the residue are replaced with lower alkyl, substituted alkyl, aryl, substituted aryl, haloalkyl, alkoxy, carbonyl, carboxy, carboxalkoxy, carboxamido, acyloxy, amidino, nitro, halo, hydroxy, $OCH(COOH)_2$, cyano, primary amino, secondary amino, acylamino, alkylthio, sulfoxide, sulfone, phenyl, benzyl, phenoxy, benzyloxy, heteroaryl, or heteroaryloxy.

An agent exhibits "specific uptake" for annulus fibrosus if it associates more frequently with, more rapidly with, for a longer duration with, or with greater affinity to, or if it is absorbed more, or accumulates more in annulus fibrosus than with non-annulus fibrosus tissues. Generally, specific uptake is characterized by a relatively high affinity of an agent to a receptor.

"FM dyes" refers to Fei Mao dyes. FM dyes are widely used to study endocytosis and vesicle trafficking in cells. FM-dyes are commonly believed to be unable to cross membranes because of their amphiphilic nature, and being anchored in the outer leaflet of the bilayer. They are thought to enter the cell primarily by endocytic vesicles invaginated from the plasma membrane. These dyes have thus been widely used as endocytosis markers. A key characteristic of FM dyes is that they are several-fold more fluorescent when dissolved in the membrane than when in an aqueous environment.

"Fibrocartilage" refers to a very strong, relatively inflexible cartilage found in the meniscus (in the knee joint), intervertebral discs, and pubic symphysis. The fibrocartilage contains cartilage of parallel, thick, compact collagenous bundles, separated by narrow clefts containing the typical cartilage cells.

"Fibrocollagenous tissue", or simply fibrous tissue refers to tissue that contains a substantial proportion of collagen. A principal feature of fibrous tissue is flexibility combined with great tensile strength. Non-limiting examples of fibrous tissue include the sclera of the eye, tendons, periosteum, ligaments and the dermis of the skin.

"Washing" generally refers to any method, such as but not limited to, immersion in, or flushing by repeated application of, a non-labeling solution or other substance, such as but not limited to water, saline, buffered saline, or ethanol, so as to provide a medium for dissociation, dispersal, and removal of unbound or non-specifically uptake labeling compound from non-annulus fibrosus tissues.

"Baseline fluorescence" refers to the frequency and magnitude of electromagnetic radiation emitted by a tissue or sample of tissue upon being exposed to an external source of electromagnetic radiation in the absence of administration or binding of any autofluorescing benzofuran compound, as distinguished from the radiation emitted following the administration and binding of such autofluorescing benzofuran compound and exposure to an external source of electromagnetic radiation.

"Normal condition of the intervertebral disc" refers to fully and normally developed disc with no changes attributable to trauma, disease, degeneration, or aging.

"Pathological conditions of the intervertebral disc" or "intervertebral discs associated-pathology" refers to changes in the intervertebral disc attributable to trauma, disease, degeneration, or aging. This includes, but is not limited to, anular tears or fissures, disc degeneration, herniated disc, protruded disc, extruded disc, and disc fragmentation.

"Parenteral administration" refers to any means of introducing a substance or compound into a subject, that does not involve oral ingestion or direct introduction to the gastrointestinal tract, including but not limited to subcutaneous injection, intraperitoneal injection, intramuscular injection, intravenous injection, intrathecal injection, intracerebral injection, intracerebroventricular injection, or intraspinal injection, or any combination thereof.

Many of the compounds described herein may comprise one or more asymmetric centers and may thus give rise to enantiomers, diastereomers, and other stereoisomeric forms that may be defined, in terms of absolute stereochemistry, as (R)— or (S)—. The chemical structure of the agent includes for example, without limitation, all such possible isomers, as well as, their racemic and optically pure forms. Optically active (R)— and (S)— isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also included.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Provided herein are methods for the qualitative or quantitative methods of imaging annulus fibrosus in a sample utilizing the specific uptake to annulus fibrosus of the compound of Formula I:

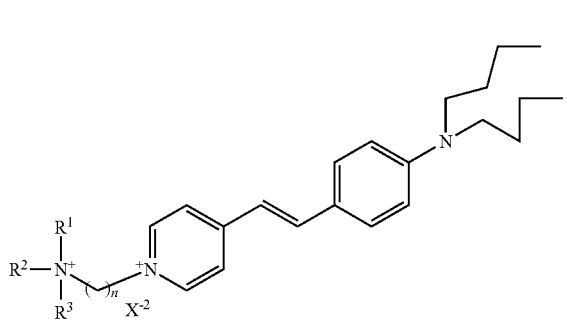

wherein $R^1$, $R^2$, and $R^3$ are each independently hydrogen, alkyl, substituted alkyl, fluroroalkyl, or perfluroalkyl, n is an integer from two to four, and X is a counter ion forming a salt. Imaging may involve auto fluorescence of the compound of Formula I, or the radioactive signal emitted by a radioisotope derivative of the compound of Formula I. In some embodiments, a radioisotope derivative of the compound of Formula I may be used and imaging accomplished through radioimaging. In some embodiments a $^{13}C$ or $^{2}H$ enriched compound of Formula I, an $^{19}F$-labeled derivative of Formula I, or a metal-DOTA (1,4,7,10-tetra-azacyclododecane-N,N',N'',N'''-tetraacetic acid) complex of Formula I, may be used. Alternatively, the compound of Formula I without modification may be used and imaged by fluorescence imaging.

The methods applicable in analytical, diagnostic, or prognostic applications related to pathological conditions of intervertebral disc and back pain are also included. These may be particularly applicable in intraoperative spinal imaging, non-invasive in vivo measurement and imaging of annulus fibrosus, and preclinical and basic neuroscience bench research aimed at the study of the function and process of annulus fibrosus degeneration, dysfunction and repair.

An agent comprising the compound of Formula I, a $^{13}C$ or $^{2}H$ enriched compound of Formula I, an $^{19}F$-labeled derivative of Formula I, a metal-DOTA (1,4,7,10-tetra-azacyclododecane-N,N',N'',N'''-tetraacetic acid) complex of Formula I, or a radioisotope derivative of Formula may be detected by its emitted signal, such as autofluorescence emission or optical properties of the agent. The method of detection of the agent may include fluorescence microscopy, laser-confocal microscopy, cross-polarization microscopy, nuclear scintigraphy, positron emission tomography ("PET"), single photon emission computed tomography ("SPECT"), chemical exchange saturation transfer imaging ("CEST"), paramagnetic chemical exchange saturation transfer imaging ("PARACEST") magnetic resonance imaging ("MRI"), magnetic resonance spectroscopy ("MRS"), computed tomography ("CT"), or a combination thereof, depending on the intended use and the imaging methodology available to the medical or research personnel.

In one embodiment, a composition comprising the compound of Formula I may be administered parenterally to a surgical subject prior to surgery involving the intervertebral discs such that the compound of Formula I binds to annulus fibrosus tissue of the intervertebral disc and may be cleared from tissues that do not contain annulus fibrosus tissue." In another embodiment, the composition comprising the compound of Formula I may be applied directly to the surgical field during surgery involving the intervertebral discs, allowed to bind to annulus fibrosus tissue present in the intervertebral discs, and the surgical site washed by lavage to clear unbound composition from the site. During surgery, a light source tuned to the spectral excitation characteristics of the compound of Formula I may be applied to the surgical field. The compound of Formula I may be observed through an optical filter tuned to its spectral emission characteristics.

Other fibrous tissue such as tendons, ligaments, and dermis of the skin, which may be present at the surgical site, do not take up the dyes. This aids in the identification of the annulus fibrosus tissue. This may assist the surgeon in the surgical treatment of the intervertebral disc by locating fluorescing tissue, or facilitates accurately administering treatment to the intended intervertebral disc.

A composition comprising the compound of Formula I may be administered parenterally to a subject prior to surgery or prior to treatments targeting intervertebral discs. In one embodiment, a composition comprising the compound of Formula I, or a $^{13}C$ or $^{2}H$ enriched compound of Formula I, or an $F^{19}$-labeled derivative of Formula I may be administered parenterally to a surgical subject, prior to surgery, to permit specific uptake to annulus fibrosus tissue, and clearance from non-annulus fibrosus tissues.

In another embodiment, a composition comprising a radioisotope derivative of the compound of Formula I may be administered parenterally to a subject prior to treatment to permit binding to annulus fibrosus tissue, and clearance from non-annulus fibrosus tissues without eliminating specific annulus fibrosus uptake. Imaging techniques such as nuclear scintigraphy, PET, SPECT, CT, MRI, MRS, or any combination thereof, may then be used to aid in differentiation of the annulus fibrosus and non-annulus fibrosus containing tissues and may employ a gamma camera, a scanner or a probe.

In another embodiment, a metal-DOTA (1,4,7,10-tetra-azacyclododecane-N,N',N'',N'''-tetraacetic acid) complex of Formula I may be administered parenterally to a subject prior to treatment to permit binding to annulus fibrosus tissue, and clearance from non-annulus fibrosus tissues without eliminating specific annulus fibrosus uptake. Imaging techniques such as nuclear scintigraphy, PET, SPECT, CEST, PARACEST, CT, MRI, MRS, or any combination thereof, may then be used to aid in differentiation of the annulus fibrosus and non-annulus fibrosus containing tissues.

The agent of a compound of Formula I may also be applied directly to the surgical filed during surgery. After binding of the composition to annulus fibrosus tissue, the surgical site may be washed by lavage to clear unbound compound from the site. During surgery a light source, tuned to the spectral excitation characteristics of the compound of Formula I, may be applied to the surgical field. The surgical field may then be observed through an optical filter tuned to the spectral emission characteristics of the compound of Formula I generating a fluorescence signal. Tissue containing annulus fibrosus that are bound by the compound of Formula I and are distinguished from tissue that do not containing annulus fibrosus thus enabling the surgeon to visually identify and pharmaceutically treat or surgically avoid other tissues.

In another embodiment, a composition comprising the radioactive derivative of a compound of a Formula I may be administered parenterally to a patient suspected of, or determined to be, suffering from a pathological condition of the intervertebral discs such as, but not limited to, anular tears or fissures, disc degeneration, herniated disc, protruded disc, extruded disc, or disc fragmentation. After uptake by annulus fibrosus tissue and clearance from non-annulus fibrosus tissue, the intervertebral discs may be imaged for in vivo using radioisotope imaging such as PET, SPECT, or any combination thereof.

By inspection of the diagnostic images, the clinician may determine if the intervertebral discs are normal or have a pathological condition. Additional scans, such as CT or MRI, may also be conducted in conjunction with PET or SPECT scans, to provide additional information, such as the structure and relative positioning of elements of the vertebral column. In one embodiment, this method may be applied to a surgical procedure to image the spinal region intraoperatively.

To determine whether annulus fibrosus in the patient may be deficient, annulus fibrosus levels may be compared to those exhibited by a subject or subjects believed or known not to be suffering from an intervertebral discs associated pathology. In another embodiment, rates of degeneration or regeneration of annulus fibrosus tissue may be determined. Following treatment with a known or suggested therapeutic agent believed or anticipated to prevent or slow degeneration or to promote regeneration in patients suffering from an intervertebral discs associated-pathology, annulus fibrosus tissue levels are evaluated by performing the imaging over time in the patients treated with the therapeutic agent. The imaging may be performed at different points of time and the level and condition of annulus fibrosus tissue at one time point compared to that of another.

In yet another embodiment, a biopsied mammalian tissue sample, or a tissue sample cultured in vitro, may be contacted with a composition comprising the compound of Formula I to determine the location, presence, or amount of annulus fibrosus tissue in the tissue sample. The tissue sample may be sampled from a subject that has been experimentally manipulated so as to serve as a verified or purported model of intervertebral discs associated-pathology, or that has received at least one therapeutic agent verified as, or purported to be, a treatment for intervertebral discs associated pathology. The therapeutic agent may be associated with the preclinical evaluation or basic neuroscience research aimed at studying the function and process of annual fibrosus tissue, and the dysfunction and repair of the tissue.

Fresh frozen cryostatic sections, or fixed or embedded sections or samples, of the biopsy or culture tissue sections, may be contacted with a composition comprising the compound of Formula I, a $^{13}C$ or $^{2}H$ enriched compound of Formula I, an $^{19}F$-labeled derivative of Formula I, a metal-DOTA (1,4,7,10-tetra-azacyclododecane-N,N',N'',N'''-tetraacetic acid) complex of Formula I, or a radioisotope derivative of the compound of Formula I. The samples may be prepared using various sectioning techniques such as microtome, vibratome, or cryostat preparation.

After specific uptake by annual fibrosus tissue, the sample may be washed in a manner and medium suitable to remove any non-specific uptake label from the sample.

Any of a number of detection, visualization, or quantitation techniques, including but not limited to fluorescence microscopy, laser-confocal microscopy, cross-polarization microscopy, autoradiography, MRI, MRS, or other applicable methods, or any combination thereof, may be then be used to assess the presence or quantity of the compound of Formula I, a $^{13}C$ or $^{2}H$ enriched compound of Formula I, an $^{19}F$-labeled derivative of Formula I, a metal-DOTA (1,4,7,10-tetra-azacyclododecane-N,N',N'',N'''-tetraacetic acid) complex of Formula I, or a radioisotope derivative of the compound of Formula I, in the tissue sample and representing the presence or amount of annulus fibrosus tissue. The labeling with, and detection, visualization, or quantitation of the compound of Formula I, a $^{13}C$ or $^{2}H$ enriched compound of Formula I, an $^{19}F$-labeled derivative of Formula I, a metal-DOTA (1,4,7,10-tetra-azacyclododecane-N,N',N'',N'''-tetraacetic acid) complex of Formula I, or a radioisotope derivative of the compound of Formula I, may also be performed in conjunction with labeling with, and detection, visualization, or quantitation of at least one other compound that specifically binds a substance other than annulus fibrosus tissue.

EXAMPLES

Reagents:

Commercially available FM lipophilic styryl fluorophores were purchased as lyophilized powders from Invitrogen (Carlsbad, Calif.) and stored at room temperature, protected from light. Fluorophores were solubilized in DMSO at a concentration of 10 mg/ml prior to experimental use and stored frozen at −80° C. Pam800 was synthesized as shown in Scheme 1 (7 wherein R'=H) from the corresponding methyl-lester-protected pamidronate (4a) using the following reagents and conditions: a) SOCl2, CH2Cl2, reflux, 1 h; b) (MeO)3P, 0° C.-RT, 30 min; c) (MeO)2P(O)H, 0° C.-RT, 30 min; d) 4, DMSO, N-methylmorpholine, RT, 4 h; e) Me3SiBr, DMF, RT, 18 h, and MeOH/H2O (4:1), RT, 30 min. R=IRDye 800CW. The Pam800 thus obtained was diluted in phosphate buffered saline, pH 7.4 (PBS) prior to intravenous (IV) administration.

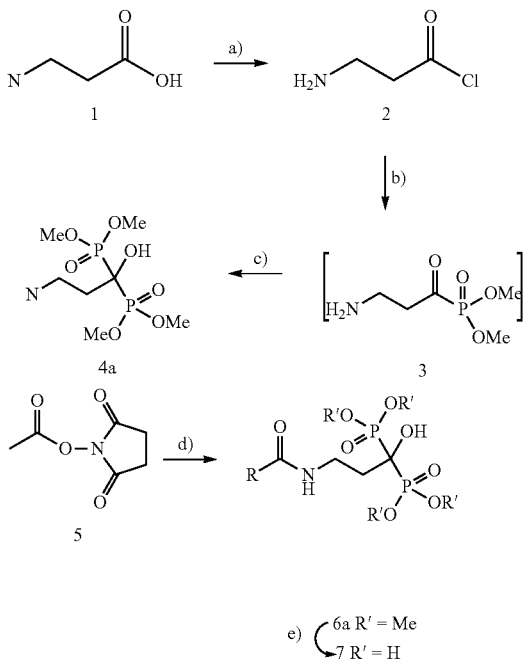

Chemical Synthesis of Formula II and Formula IA

Formula II and IA were synthesized by the condensation of N-alkyl-4-picolinium salts with 4-N-dibutylamino benzaldehyde and 1-(4-N-dibutylaminophenyl)-1,3-pentadien-5-al, respectively (Schemes 2 and 3). Formula IA is Formula I wherein $R^1$, $R^2$ and $R^3$ are $CH_3$, n is three, and X is Br.

Figure 2A:
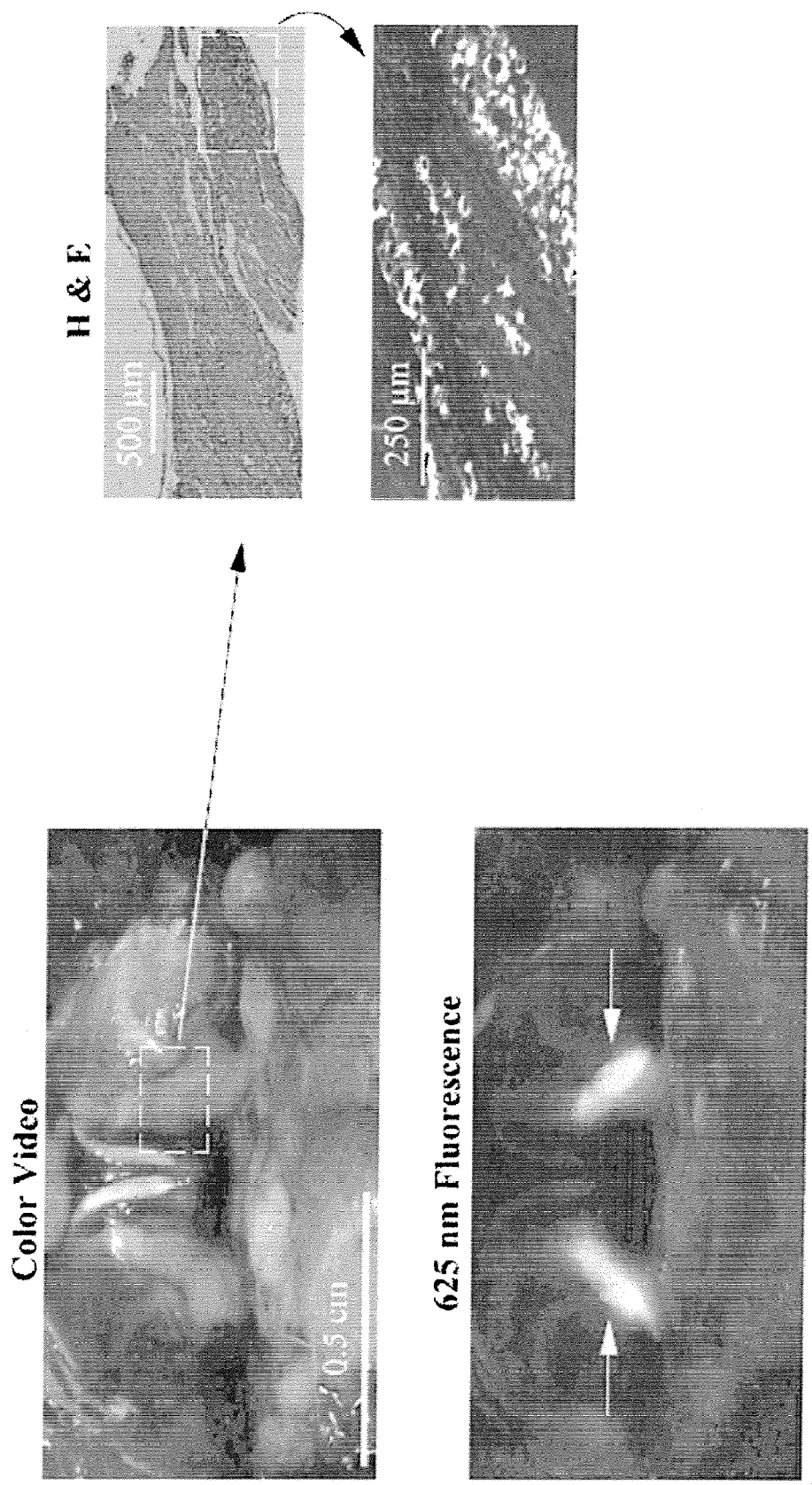
FIG. 2 shows in vivo Imaging of dorsal nerve root ganglia and trigeminal nerves of a mouse and a rat.

The required picolinium salts were prepared by the alkylation of 4-picoline with the corresponding 3-bromopropyl-trialkyl ammonium bromide. Ring opening of pyridine with cyanogens bromide gave the iminium salt 1, which was hydrolyzed in the presence of sodium hydroxide to the vinylogous amid 2 (FIG. 2A). The vinylogous amid 2, was used in a Vilsmeir-Haack-like formylation of N,N-dibutylaniline to produce the desired 1-(4-N-dibutylaminophenyl)-1,3-pentadien-5-al, 3.

Scheme 2

Scheme 3

(E)-N-methyl-N((2E,4E)-5-(methyl(phenyl)amino) penta-2,4-dienylidene)benzenaminium bromide (1)

To a solution of N-methylaniline (30 g, 140 mmol) and pyridine (11.2 g, 140 mmol) in diethylether (100 ml) at 0° C., was added a solution of cyanogen bromide (14.8 g, 140 mmol) in ether (40 ml) dropwise. The mixture was warmed to 20° C. and within 15 minutes a red oil began to separate. Exothermic (30° C.) crystallization ensued and the red solid mass was left to stand at room temperature overnight. The crystalline mass was filtered and washed with cold ether under $N_2$ and the hygroscopic salt was used in the next step without further purification. Yield: 47.7 g (95%).

(2E,4E)-5-(methyl(phenyl)amino)penta-2,4-dienal (2)

A solution of the salt described above (47.7 g) in methanol (240 ml) was added to a mixture of sodium hydroxide (6.2 g, 1.15 eq.), water (36 ml) and MeOH (85 ml). After the addition, enough water was added to keep the mixture just shy of forming a light-yellow precipitate (cca 300-350 ml water). The clear mixture was stirred at 30° C. for 2 hours, at which time TLC analysis (EtOAc, silicagel 60) indicated complete conversion. The mixture was poured over saturated brine (1.2 L) at 15° C. and extracted with benzene/Et2O 1/1 v/v (cca 550 ml). The extract was thoroughly dried (Na2SO4 filtered off the drying agent, and diluted with petroleum ether (b.p. 35-60° C.)). Upon the addition of 1.2 L a light yellow oil began to separate, which precipitated in long yellow needles. As the crystallization proceeded, more petroleum ether (1.2 L) was added gradually and the mixture was stored at −20° C. overnight, then filtered and dried. Yield: 21.8g (87%). MS (ESI+): 188(M+H+); 210 (M+Na+); 229 (M+H++CH3CN).

(2E,4E)-5-(4-(dibutylamino)phenyl)penta-2,4-dienal (3)

To a solution of the vinylogous amide 2 (1.135 g, 6.06 mmol) and dibutylaniline (1.43 g) in dry THF (6 ml) at −20° C. was added a solution of phosphorus oxychloride (1.08 g, 1.17 eq.) and dibutylaniline (1.03 g, 1.98 eq. for the sum) in THF (3.6 ml) dropwise at such a rate as to keep the mixture between −10° C. and −20° C. Following the addition, the mixture was stirred at room temperature for 2 hours and at 50° C. for 35 minutes. To the reaction mixture (a dark blue-green oil) was added petroleum ether (25 ml) and the mixture was triturated; the ether was separated and discarded. Methanol (4 ml) was then added and the mixture was neutralized with 2N NaOH. Silicagel was then added, the suspension was diluted with ethyl acetate and methanol and dried to a solid on the rotovap. The crude product was purified by MPLC using hexanes-ethyl acetate 5-30% gradient to give the desired aldehyde as an intense yellow oil (225 mg, 13%). MS (EI): 285 (M+, 45%); 242 (100%); 200 (85%); 128 (30%); 118 (40%). H-NMR (CDCl3): 0.95 (t, J=12 Hz, 6H); 1.35 (m, 4H); 1.45 (m, 4H); 3.8 (t, J=9 Hz, 4H); 6.4, (d, J=17 Hz, 1 H); 6.5-6.8 (m, 3H); 7.1 (d, J=15 Hz,1 H); 7.5 (d, J=17 Hz,1 H); 7.8 (d, J=11 Hzm 2H); 9.8 (s,1 H).

4-Methyl-1-(3-(triethylammonio)propyl)pyridinium dibromide (4)

To an N2-flushed vial was added 3-bromopropyltrimethyl ammonium bromide (5.138 g, 13.56 mmol) and 4-picoline (1.27 g, 1 eq.) and the mixture was heated to 125° C. in a tetraethylene glycol bath. The mixture became homogeneous in 5 minutes and a salt started precipitating in 15 minutes. After 35 minutes of reaction time, the mixture was dissolved in boiling methanol (8 ml) and layered with tetrhydrofuran. The crystals were washed (4×) with cold THF and dried in a vacuum. Yield: 4.45 g (86%). MS (EI+): 111 (M+H)2+

4-((1 E,3E,5E)-6-(4-(dibutylamino)phenyl)hexa-1,3, 5-trienyl)-1-(3-(triethylammonio)propyl)pyridinium dibromide (5) (FORMULA II)

To a dry vial was added the salt 2 (578 mg, 1.46 mmol), the aldehyde 4 (416 mg, 1.46 mmol) and the vial was purged with N2. Ethanol (7.5 ml) was added via syringe, followed by piperidine (0.75 ml). The mixture was stirred at room temperature for 12 hours and concentrated, and the salt was precipitated with dry ether. Following solvent removal, the salt was again dissolved in EtOH (8 ml) and precipitated with ether. The resulting fluorophore was filtered under a nitrogen atmosphere and dried. MS (MALDI and dual ESI+): 582.342 (C34H53N3Br)+ (calculated 582.3412); 251.712 (C34H53N3)2+ H-NMR (DMSO-D6): 0.9 (t, J=12 Hz, 6H); 1.22-1.40 (m, 13H); 1.52 (m, 4H); 2.23 (m, 2H); 3.18-3.35 (m, 8H); 3.82 (t, J=10 Hz, 4H); 4.20 (t, J=12 Hz, 2H); 6.65-6.72 (m, 4H); 6.82 (m, 3H); 7.12 (d, J=18 Hz, 2H); 7.85 (d, J=8 Hz, 2H); 8.1 (d, J=6 Hz, 2H); 8.90 (d, J=6 Hz, 2H).

4-Methyl-1-(3-(trimethylammonio)propyl)pridinium dibromide (6)

To a $N_2$-flused vial was added 3-bromopropyltrimethyl ammonium bromide (4.972 g, 18.5 mmol) and 4-picoline (1.82 ml, 18.5 mmol) and the mixture was heated to 125° C. in a tetraethyleneglycol bath. The mixture became homogeneous in 5 minutes and a salt started precipitating in 15 minutes. After 35 minutes of reaction time, the mixture was dissolved in boiling methanol (8 ml) and layered with tetrahydrofuran. The crystals were washed (4×) with cold THF and dried in a vacuum. Yield: (5.78 g (92%). MS (ESI+): m/z: 90 (M+H)2+

(E)-4-(4-(dibutylamino)styryl)-1-(3-(trimethylammonio)propyl)pyridinium dibromide (7) (FORMULA IA)

To a dry vial was added the salt 6 (708 mg, 2 mmol), 4-dibutylaminobenzaldehyde (467 mg, 2 mmol) and the vial was purged with N2. Ethanol (10 ml) was added via syringe, followed by piperidine (1 ml). Within 5 minutes the color began changing to deep red. The mixture was stirred at room temperature for 12 hours, concentrated and the salt was precipitated with dry ether. Following solvent removal, the salt was again dissolved in EtOH (8 ml) and precipitated with ether. The resulting fluorophore was filtered under a nitrogen atmosphere and dried. Yield: 1.04 g (91%). MS (dual ESI+): 204.69186 (M+H+)2+ HRMS calc. 409.3457. H-NMR (DMSO-D6): 0.92 (t, J=12 Hz, 6H); 1.38 (m, 4H); 1.48 (m, 4H); 2.24 (m, 2H); 3.22/-3.35 (m, 11 H); 3.85 (t, J=9 Hz, 4H); 4.25 (t, J=12 Hz, 2H); 6.8 (d, J=8 Hz, 2H); 6.97 (s, 2H); 7.75 (d, J=8 Hz, 2H); 8.05 (d, J=6 Hz, 2H); 8.95 (d, J=6 Hz, 2H).

Preparation of Radioactive Derivatives

Based on the X-1-1 motif, FM dyes having an available primary amine may be converted into a SPECT, PET, or MRI agent using the following methods. For SPECT agents, conjugation of pre-labeled $^{99m}$Tc-MAS3-NHS or post-labeling with $^{99m}$Tc- after conjugation of MAS3-NHS to form a stable amide bond. Alternatively, any of several conjugation techniques and chelators besides NHS or MAS3 may be used. For PET agents, conjugation of derivatized $^{18}$F-FDG using lactone chemistry to form a stable amide bond, or one of several other $^{18}$F-labeling techniques may be used. For MRI agents, conjugation of pre-labeled DOTA-Gd3+-NHS or post-labeling with Gd3+ after conjugation of DOTA-NHS to form a stable amide bond may also be used.

Preparation of Metal-DOTA Complexes

Based on the X-1-1 motif FM dyes having an available primary amine may be conjugated with a DOTA derivative such as a mono-(N-hydroxysuccinimide ester) (DOTA-NHS-ester) under anhydrous conditions in the presence of a millieq excess of a base such as triethylamine. The DOTA amide thus formed may then be complexed with a lanthanide metal such as Gd+3, Sm+3, Pr+3, Eu+3, Tb+3, Dy+3, Dy+3, Ho+3, Er+3, Tm+3, Yb+3, and Lu+3.

In Vitro Characterization of FM Fluorophores:

Absorbance and fluorescence spectra of the FM fluorophores were measured in PBS and absolute methanol (MeOH) using fiber-optic HR2000 (200-1100 nm) and USB2000FL (350-1000 nm) spectrometers (Ocean Optics, Dunedin, Fla.), respectively. Fluorescence excitation was provided by a 2 mW, 532 nm laser diode. The fluorescence and absorbance spectra of FORMULA II and FORMULA IA were collected in dimethyl sulfoxide (DMSO) and fetal bovine serum (FBS), as well as MeOH and PBS. The quantum yield of FORMULA II and FORMULA IA in DMSO, MeOH, FBS and PBS was measured by comparing the integrated fluorescence emission of the fluorophores in each solvent to the emission of Alexa Fluor 555 (Invitrogen) in PBS (quantum yield=10%) as a reference standard under conditions of matched absorbance at the excitation wavelength. The LogD of each FM fluorophore at pH 7.5 was calculated using Marvin 5.0.3 software (ChemAxon, Budapest, Hungary).

Animals:

CD-1 mice of either sex weighing 28 to 30 grams and Sprague-Dawley rats of either sex weighing 250 to 300 grams were purchased from Charles River Laboratories (Wilmington, Mass.). A female Yorkshire pig weighing 35 kg was purchased from E. M. Parsons & Sons (Hadley, Mass.). Prior to surgery, mice and rats were anesthetized with 65 mg/kg intraperitoneal (IP) pentobarbital (Ovation Pharmaceutical, Inc., Deerfield, Ill.). Pig anesthesia was induced with 4.4 mg/kg intramuscular Telazol® (Fort Dodge Labs, Fort Dodge, Iowa), intubated, and maintained with 2% isoflurane.

Intraoperative Fluorescence Imaging System:

Imaging was carried out at near infrared wavelenghts using a 400- to 700-nm "white" light (0.5 mW/cm$^2$) and a 725- to 775-nm NIR fluorescence excitation light (5 mW/cm$^2$). Fluorescence images were collected using exposure times ranging from 500 to 2000 msec. All images collected for comparison between vehicle-injected control animals and FM fluorophore-injected animals had the same exposure time and normalization. Color video images were collected on a separate optical channel using custom designed software. The excitation and emission LEDs and filter used for the FM fluorophores and Pam800 in the intraoperative imaging system are described as follows. For fluorescence excitation of FM 1-43, FM 2-10, FM 1-43FX and Formula IA, sixty 5-mm 470 nm LEDs (Epitex, Inc., Kyoto, Japan) fitted with 470±20 nm band pass (BP) excitation filters (Chroma Technology, Rockingham, Vt.) in custom holders were used, which produced a fluence rate on the imaging surface of 0.56 mW/cm$^2$. For fluorescence excitation of Formula II, FM 4-64, FM 4-64FX and FM 5-95, sixty 5-mm 535 nm LEDs fitted with 525±25 nm BP excitation filters were used, which produced a fluence rate on the imaging surface of 0.34 mW/cm$^2$. A 610±38 nm BP filter was used to detect fluorescence emission of FM 1-43, FM 2-10, Formula II, FM 1-43FX and Formula IA. To detect fluorescence emission of FM 4-64, FM 4-64FX and FM 5-95 a 720 nm long pass (LP) filter was used. For fluorescence excitation of Pam800, 348 5-mm 760 nm LEDs fitted with 764±17 nm BP excitation filters were used, which produced a fluence rate on the imaging surface of 8.73 mW/cm$^2$ and fluorescence emission was detected using a 824±24 nm BP emission filter.

Formulation, Dosing, and Kinetics for In Vivo Fluorescence Imaging:

To assess the structure-activity relationship of the FM fluorophores, each molecule was administered at 5 mg/kg to mice and 0.5 mg/kg to rats (n=4 per group) in 10% DMSO and 90% PBS IP 16 hours before imaging with the intraoperative system. The fluorescence signal from the spinal cord, intervertebral discs, dorsal root ganglia, trigeminal ganglia, optic nerve, brain and femoral nerve were normalized to muscle signal in the same image. This normalization ratio was then compared between FM fluorophore-injected animals and vehicle-injected control animals. Positive contrast was concluded if the nerve-to-muscle contrast ratio of FM fluorophore-injected animals was elevated relative to control animals.

Administration of 2 mg/kg of FORMULA IA, resuspended in 5% DMSO and 95% PBS, IV 2 to 4 hours prior to imaging was found to produce similar contrast ratio to the 5 mg/kg IP administration 16 hours before imaging. FORMULA IA (2 mg/kg IV) and Pam800 (7.5 nmol in 500μl of PBS IV) were administered to a male Sprague-Dawley rat for enhanced visualization of the intervertebral discs. Pam800 was administered 12 hours prior to FORMULA IA. Four hours after administration of FORMULA IA the animal was sacrificed and its spine was removed. The spine was imaged simultaneously for Pam800 and FORMULA IA fluorescence; color video was also obtained at the same time.

FORMULA IA was also evaluated in a Yorkshire pig. The administered dose of FORMULA IA was scaled from the mouse to the pig by body surface area where the body surface area of the pig was estimated to be 271.7 times larger than the mouse translating to a dose of 0.47 mg/kg. FORMULA IA was administered IV in 5% DMSO and 95% PBS to an anesthetized pig 5 hours before imaging. The pig was monitored under anesthesia during the drug incubation period, after which the animal was sacrificed. The spine was imaged in vivo for FORMULA IA, then removed and sectioned for further imaging.

In Vivo Optical Spectroscopy:

FORMULA II and FORMULA IA were evaluated in different mice by imaging their trigeminal ganglia with a Maestro™ small animal multi-spectral imaging system (CRI, Woburn, Mass,). Agents were administered at 2 mg/kg in 5% DMSO and 95% PBS IV. At 4 hours mice were anesthetized and sacrificed, and their trigeminal ganglia were exposed for imaging. A 467±23 nm filter was used for excitation; the fluorescence emission spectra were collected between 515 and 1000 nm at 10 nm intervals. The in vivo fluorescence spectra of FORMULA II and FORMULA IA in the trigeminal ganglia were unmixed from the spectral signature of nearby muscle tissue using the software supplied by the manufacturer.

Histology and Microscopy:

Tissues from mice, rats and pig were preserved for microscopic assessment and localization of fluorescence signal. Tissues were extracted from the animal and placed in 2% paraformaldehyde in PBS for 2 to 4 hours before mounting in Tissue-Tek OCT compound (Fisher Scientific, Pittsburgh, Pa.

) and flash-freezing in liquid nitrogen. Each sample was cryosectioned (12 μm per slice); one slide was stained with hematoxylin and eosin (H&E) and a consecutive section was used for fluorescence microscopy. For fluorescence microscopy, serial sections were imaged on a Nikon TE 300 microscope system equipped with a mercury excitation source (Chiu Technical Corporation, Kings Park, N.Y.), Orca-ER 12-bit camera (Hamamatsu, Bridgewater, N.J.), and IPLab software (BD Biosciences, Rockville, Md.), using the following excitation and emission filters combinations. To obtain fluorescence images of FM 4-64, the mercury light source was passed through a 540±15 nm BP excitation filter, 700 nm dichroic beam splitter and 720 nm LP emission filter. To obtain fluorescence images of FM 1-43FX and Formula IA, the mercury light source was passed through a 460±25 nm BP excitation filter, 505 nm dichroic beam splitter and a 610±38 nm BP emission filter. Exposure times were adjusted between 5 and 2000 ms for fluorescence images.

Results and Observations:

FM Fluorophore Nomenclature and Properties: The chemical structures of FM fluorophores enable division of each molecule into left, middle and right groups (Table 1). Each group has two or three available chemical motifs, resulting in twelve possible FM fluorophores. FM fluorophores shown in Table 2 were tested.

The fluorophores FM 1-43, FM 1-43X, and Formula IA are compounds of Formula I. FM 1-43 is Formula I wherein $R^1$, $R^2$ and $R^3$ are $C_2H_5$, n is equal to 3, and X is equal to Br. FM1-43X is Formula I wherein $R^1$ and $R^2$ are equal to $CH_3$, $R^3$ is equal to $C_3H_6NH_3+Cl-$, n is equal to 3, and X is Cl. Formula IA is Formula I wherein $R^1$, $R^2$ and $R^3$ are $CH_3$, n is three, and X is Br.

The physicochemical and optical properties of the eight FM fluorophores are shown in Table 3. All fluorophores had molecular weights ranging from 550 to 800 Daltons, and a negative LogD at neutral pH (except for FORMULA II). All fluorophores exhibited red-shifted excitation maxima in MeOH compared to PBS, but most emission maxima were similar in both solvents. FM fluorophores with the chemical structure x-2-x had significantly red-shifted emission compared to those with the structure x-1-x.

TABLE 2

FM Fluorophore Chemical Structures and Nomenclature Notation

| Name | Notation | Left | Middle | Right |
|---|---|---|---|---|
| FM 1-43 | 1-1-1 | 1 | 1 | 1 |
| FM 2-10 | 1-1-2 | 1 | 1 | 2 |
| Formula II | 1-2-1 | 1 | 2 | 1 |
| FM 4-64 | 1-2-2 | 1 | 2 | 2 |
| FM 1-43FX | 2-1-1 | 2 | 1 | 1 |
| FM 4-64FX | 2-2-2 | 2 | 2 | 2 |
| Formula IA | 3-1-1 | 3 | 1 | 1 |
| FM 5-95 | 3-2-2 | 3 | 2 | 2 |

TABLE 3

FM Fluorophore Physicochemical and Optical Properties

| Name | Notation | Molecular Weight | Log D (pH 7.5) | Ex/Em nm (PBS) | Ex/Em nm (MeOH) |
|---|---|---|---|---|---|
| FM 1-43 | 1-1-1 | 611.6 | −1.0 | 493/631 | 509/624 |
| FM 2-10 | 1-1-2 | 555.4 | −2.7 | 490/628 | 507/622 |
| Formula II | 1-2-1 | 611.5 | 0.1 | 519/808 | 549/813 |
| FM 4-64 | 1-2-2 | 607.5 | −1.7 | 507/808 | 546/811 |
| FM 1-43FX | 2-1-1 | 560.1 | −5.3 | 490/628 | 511/622 |
| FM 4-64FX | 2-2-2 | 788.8 | −5.9 | 509/815 | 531/808 |
| Formula IA | 3-1-1 | 569.5 | −2.0 | 497/628 | 510/624 |
| FM 5-95 | 3-2-2 | 565.4 | −2.7 | 490/809 | 542/809 |

Figure 1B:
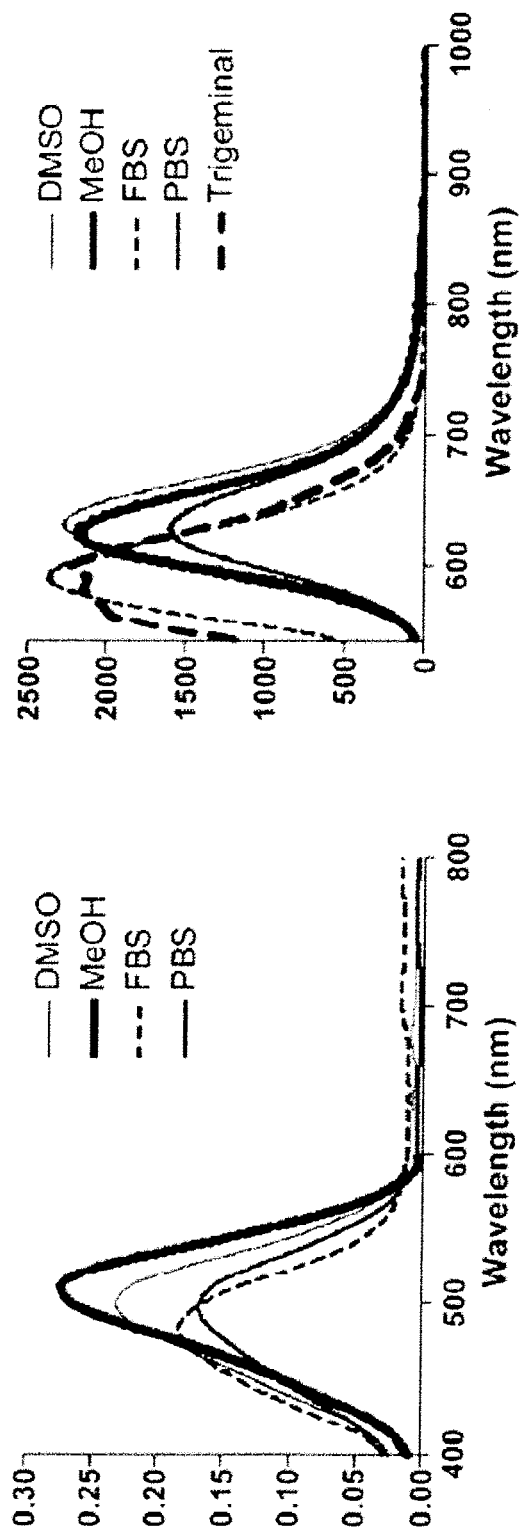

Spectral and Chemical Characterization of Novel FM Fluorophores:

The spectral properties of FORMULA II and FORMULA IA were investigated in solvents with varied proton content, including DMSO, MeOH, FBS and PBS (FIG. 1). The emission spectrum of FORMULA II was significantly affected by solvent environment, as its emission maximum was blue-shifted over 100 nm when diluted in FBS compared to DMSO, MeOH or PBS (FIG. 1A). The emission spectrum of FORMULA IA was less affected by solvent, as its emission maximum was blue-shifted 35 to 40 nm in FBS as compared to DMSO, MeOH, or PBS (FIG. 1B). The extinction coefficient was also distinct in the four solvents, with the extinction coefficient largest for both fluorophores in DMSO and MeOH as compared to FBS or PBS. The fluorescence quantum yield

TABLE I

FM fluorophores composition by structural unit defined as left, right, and middle position.

was highest in FBS for both synthesized fluorophores, being 5 times higher in FBS for Formula I, and 10 times higher in the same solvent for Formula II. The spectral properties of both fluorophores were characterized in vivo in the trigeminal ganglia of mice. The emission spectra of both FORMULA II and FORMULA IA were most similar to the emission spectra of the fluorophores in FBS (FIG. 1).

Tissue-Specific Uptake In Vivo and Structure-Activity Relationships:

dashed rectangles) 810 nm fluorescence images of consecutive unstained histological sections. Data are representative of n=4 independent experiments.

Only three of the eight FM fluorophores, FM 1-43, FM 1-43FX and FORMULA IA, showed positive contrast in the intervertebral discs (Table 4), and each of these fluorophores had the motif labeled "1" in the middle and right positions (Table 2). The positive contrast in the intervertebral disc may be generalized into the following notation x-1-1. In contrast,

TABLE 4

Results of FM fluorophores uptake studies, fluorophores are identified by name and shorthand notation corresponding to the chemical group.

| | Notation | Dorsal Root Ganglia | Spinal Cord | Intervertebral Disc | Trigeminal Ganglia | Optic Nerve | Brain | Femoral Nerve |
|---|---|---|---|---|---|---|---|---|
| FM 1-43 | 1-1-1 | + | − | + | + | − | − | − |
| FM 2-10 | 1-1-2 | − | − | − | + | − | − | − |
| Formula II | 1-2-1 | − | − | − | + | − | − | − |
| FM 4-64 | 1-2-2 | + | − | − | + | − | − | − |
| FM 1-43FX | 2-1-1 | + | − | + | + | − | − | − |
| FM 4-64FX | 2-2-2 | + | − | − | + | − | − | − |
| Formula IA | 3-1-1 | + | − | + | + | − | − | − |
| FM 5-95 | 3-2-2 | + | − | − | + | − | − | − |

The simplest nontoxic and biocompatible IV formulation found to maximize FM fluorophore solubility (up to a 26.3 mM stock solution) was 5% DMSO and 95% PBS (data not shown). In preliminary experiments, the kinetics and dose response of FORMULA IA were evaluated in mice. FORMULA IA was administered at 1 and 2 mg/kg IV in 5% DMSO and 95% PBS 16, 8, 4 and 2 hours prior to imaging. Similar contrast was seen when FORMULA IA was administered at 2 mg/kg IV, 2 and 4 hours prior to imaging, or at 5 mg/kg IP, 16 hours prior to imaging.

After IP administration to mice and rats, all agents showed positive contrast in the trigeminal ganglia (TG), but none in the optic nerve or brain (Table 4). Black and white versions of a color video and 625 nm fluorescence images of the trigeminal ganglia (TG; arrows) in a mouse administered 5 mg/kg FM 1-43FX (2-1-1) 16 h post-IP injection is shown in FIG. 2A (ON=optic nerves. BR=brain). Shown at right in FIG. 2A is H&E histology for the area indicated by a white dashed rectangle, along with zoomed (within white dashed rectangles) 625 nm fluorescence images of consecutive unstained histological sections. Data are representative of n=4 independent experiments. When the same nerve was examined microscopically, the densely cellular areas identified by H&E staining had the strongest fluorescence signal (FIG. 2A). All FM fluorophores, except FM 2-10 and FORMULA II, also showed positive contrast in the dorsal root ganglia in mice and rats.

Figure 2B:
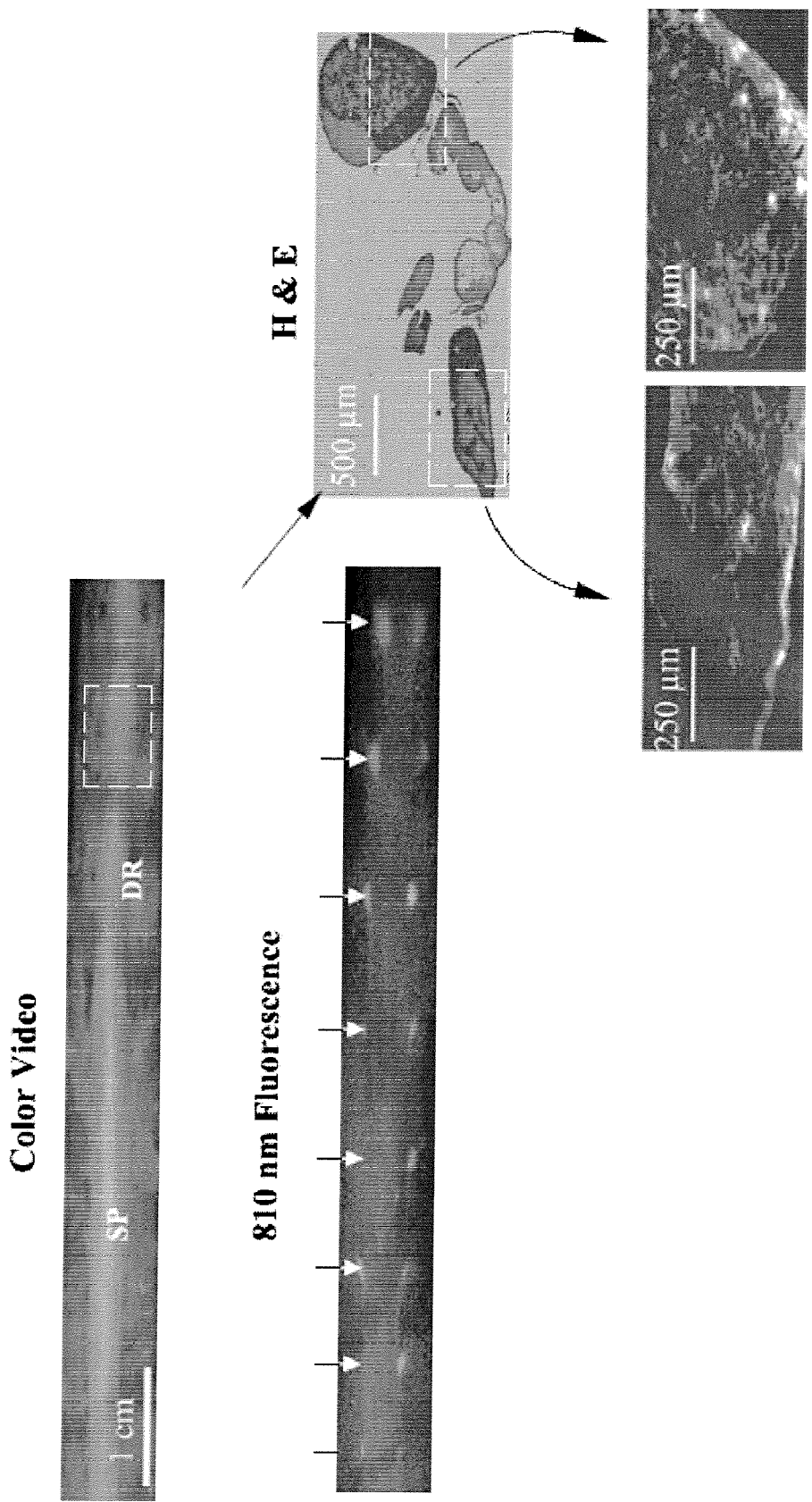

A rat administered FM 4-64 is shown in FIG. 2B, where the spine was cross-sectioned ex vivo so that two dorsal root ganglia were visible in a single tissue section. Similar to the trigeminal ganglia, when examined microscopically, significant fluorescence intensity was seen in the dense cellular regions of each dorsal root ganglion (FIG. 2B). FIG. 2B is a black and white version of a color video and 810 nm fluorescence images of dorsal nerve root ganglia (DR; arrows) 16 h post-IP injection of 0.5 mg/kg FM 4-64 (1-2-2). (SP=spine). Shown at right is a H&E histology for the area indicated by a white dashed rectangle, along with zoomed (within white six of the eight FM fluorophores showed positive contrast in the dorsal root ganglia. The two FM fluorophores that did not show positive contrast in the dorsal root ganglia did not have the same middle and right motif (Table 4), thus the property for positive contrast in the dorsal root ganglia may be generalized into the following notation x-i-i, where i=1 or 2. All eight of the tested FM fluorophores showed positive contrast in the trigeminal ganglia.

Figure 3:
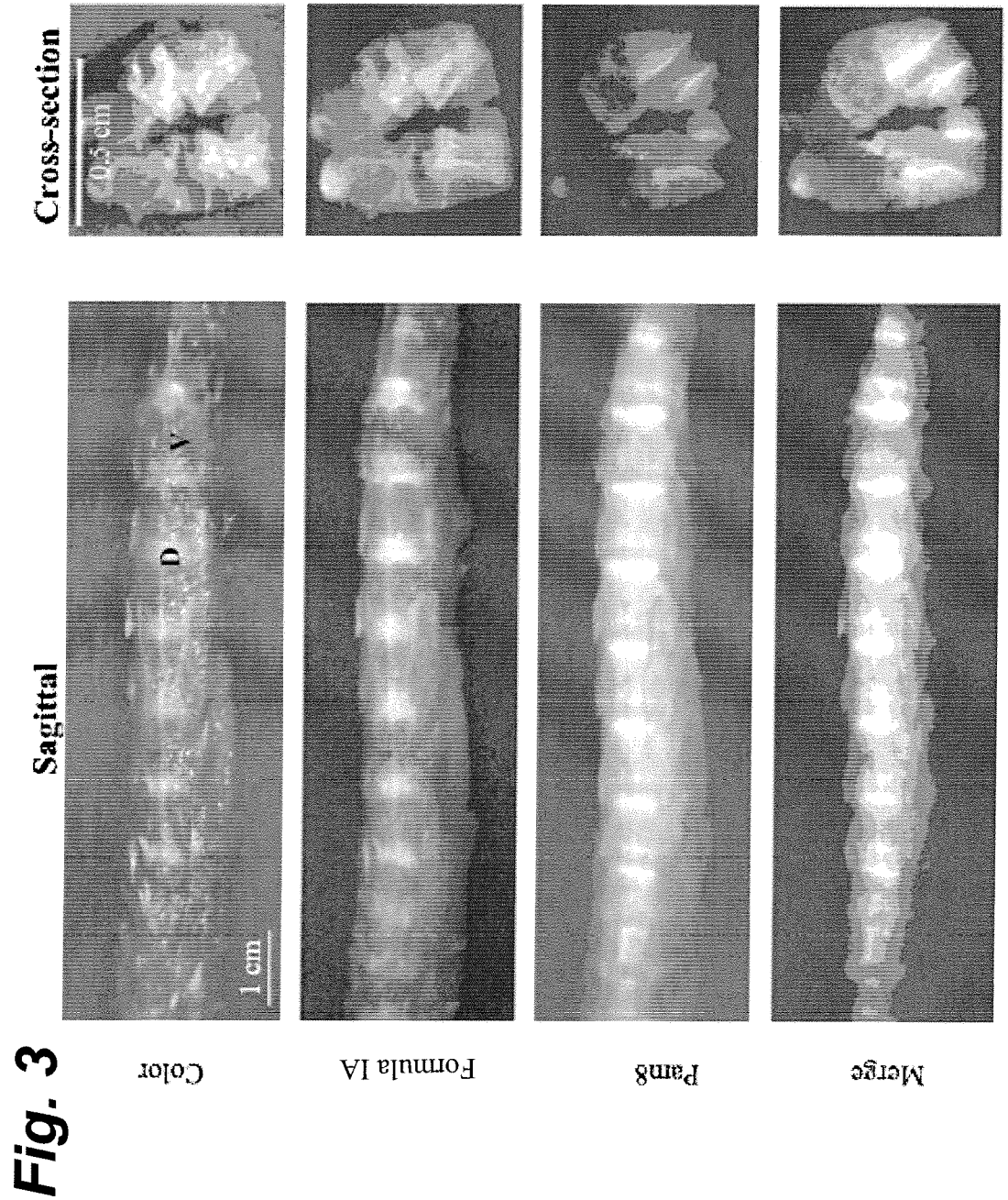
FIG. 3 shows a simultaneous, two-wavelength imaging of the vertebrae and intervertebral disks of a resected spine of a rat.

Intervertebral Disc Fluorescence:

The uptake of FM 1-43, FM 1-43FX and FORMULA IA into intervertebral discs was investigated in more detail. Pam800 a near-infrared fluorophore specific for hydroxyapatite of bone, was co-injected with FORMULA IA to ensure that the fluorescence signal seen in the spine was originating in the discs and not in the bone. As illustrated in FIG. 3, FORMULA IA was specific for the intervertebral discs, which was seen when the disc was observed in situ in the sagittal spine as well as when an individual disc was observed in cross-section. There was no overlap of pseudo-colored signals from Pam800 and FORMULA IA. FIG. 3 is a resected spine of a rat, 16 h post-IV injection of 7.5 nmol Pam800 and 4 h post-IV injection of 2 mg/kg Formula IA (3-1-1). Shown are black and white versions of a color video image (top), 600 nm fluorescence for Formula IA (3-1-1; 2nd row), 800 nm fluorescence for Pam800 (3rd row), and a pseudo-colored (original green for Pam800; red for Formula IA (3-1-1) reproduced in black and white) of the two (bottom), as a sagittal section (left) or cross-section (right). Data are representative of n=3 independent experiments.

Figure 4:
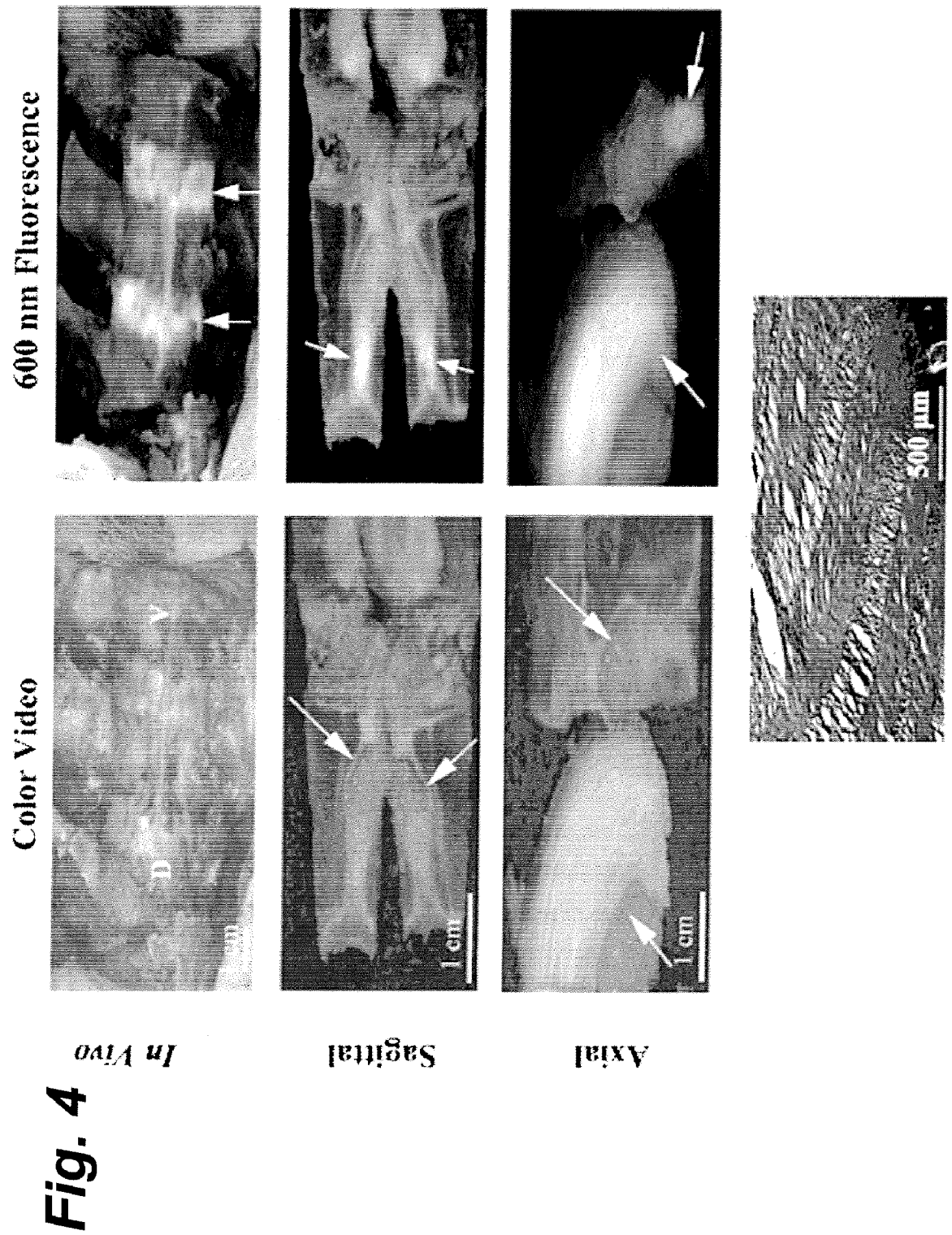
FIG. 4 shows a real-time intraoperative imaging of the annulus fibrosus in a pig.

Species dependency of FORMULA IA was further investigated in the pig. As shown in FIG. 4, a dramatic positive contrast was detected in the intervertebral discs. Sagittal and axial sectioning confirmed that the majority of the signal was emanating from the annulus fibrosus, and not the nucleus pulposus. When disc sections were examined microscopically, the fluorescence pattern was punctate and linear following the lamellae structures of the annulus fibrosus, and corresponding to cell-rich areas seen by H&E. FIG. 4 is a black and white version of a color video (left) and 600 nm fluorescence (right) in a pig 5 h post-IV injection of 0.47 mg/kg Formula IA. D=intervertebral disks. V=vertebrae. Arrows indicated annulus fibrosus. Arrowheads indicate nucleus pulposus. After en bloc surgical resection, sagittal and axial images of the spine were acquired. Also shown (bottom) is H&E of the annulus fibrosus from the same specimen.

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

The invention claimed is:

1. A method of annulus fibrosus imaging comprising:
administering to a subject an agent wherein the agent comprises a compound of Formula I, a $^{13}$C or $^2$H enriched compound of Formula I, an $^{19}$F-labeled derivative of Formula I, a metal-DOTA (1,4,7,10-tetra-azacyclododecane-N, N', N", N'''-tetraacetic acid) complex of Formula I, or a radioisotope derivative of Formula 1

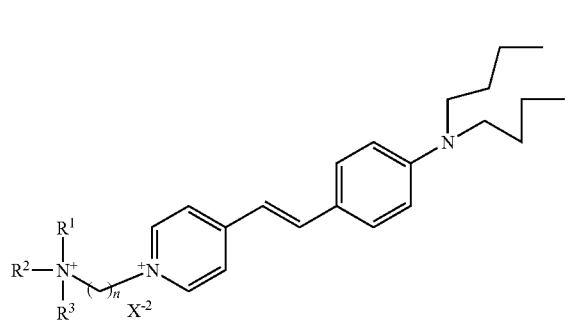

I wherein $R^1$, $R^2$, and $R^3$ are each independently hydrogen, alkyl, substituted alkyl, fluroroalkyl, or perfluroalkyl, n is an integer from two to four, and X is a counter ion forming a salt; and
selectively imaging annulus fibrosus by detecting the agent present in annulus fibrosus tissue.

2. The method of claim 1 wherein $R^1$, $R^2$, and $R^3$ are equal to $CH_3$, n is equal to three, and X is Br.

3. The method of claim 1, wherein the radioisotope derivative contains a radioisotope label selected from $^3$H, $^{11}$C, $^{14}$C, $^{18}$F, $^{32}$, $^{35}$S, $^{123}$I, $^{125}$I, $^{131}$I, $^{36}$CI, and $^{75}$Se.

4. The method of claim 3, wherein the radioisotope label is selected from $^3$H, $^{11}$C, $^{14}$C, and $^{18}$F.

5. The method of claim 1 wherein the metal-DOTA complex is chelated to a metal selected from Gd+3, Sm+3, Pr+3, Eu+3, Tb+3, Dy+3, Dy+3, Ho+3, Er+3, Tm+3, Yb+3, and Lu+3.

6. The method of claim 1 wherein the metal-DOTA complex is chelated to a radisotope selected from $^{111}$In, $^{64}$Cu, $^{86}$Y, and $^{52}$Fe.

7. The method of claim 1 wherein the parenteral administration comprises intravenous injection, intraperitoneal injection, subcutaneous injection, intramuscular injection, intrathecal injection, intracerebral injection, intracerebroventricular injection, intraspinal injection, or combinations thereof.

8. The method of claim 1 wherein the detecting is effected by gamma imaging.

9. The method of claim 8 wherein the gamma imaging is nuclear scintigraphy, PET, SPECT, or a combination thereof.

10. The method of claim 1 wherein the detecting is effected by MRI, MRS, CEST, PARACEST, or a combination thereof.

11. The method of claim 1 further comprising the step of quantifying the amount of the agent in the subject.

12. The method of claim 11 wherein the quantifying step comprises measuring radioactivity of agent and wherein the agent comprises the radioactive derivative of Formula I bound to the tissue sample.

13. A method of imaging annulus fibrosus tissue in a surgical field comprising the steps of:
contacting the surgical site with an agent, wherein the agent comprises a compound of Formula I, a $^{13}$C or $^2$H enriched compound of Formula I, an $^{19}$F-labeled derivative of Formula I, a metal-DOTA (1,4,7,10-tetra-azacyclododecane-N, N', N", N'''-tetraacetic acid) complex of Formula I, or a radioisotope derivative of Formula 1

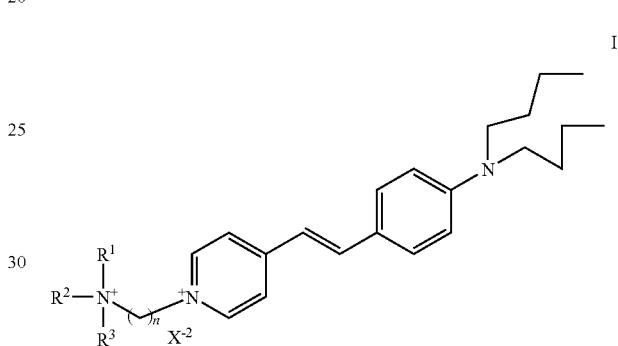

I wherein R1, R2, and R3 are each independently hydrogen, alkyl, substituted alkyl, fluroroalkyl, or perfluroalkyl, n is an integer from two to four, and X is a counter ion forming a salt; and
detecting the agent by imaging annulus fibrosus tissue.

14. The method of claim 13 wherein $R^1$, $R^2$, and $R^3$ are equal to $CH_3$, n is three, and X is Br.

15. The method of claim 13 wherein the surgical site is an open surgical field or a minimally invasive field.

16. The method of claim 13, wherein the radioisotope derivative contains a radioisotope label selected from $^3$H, $^{11}$C, $^{14}$C, $^{18}$F, $^{32}$P, $^{35}$S, $^{123}$I, $^{125}$I, $^{131}$I, $^{36}$CI, and $^{75}$Se.

17. The method of claim 16, wherein the radioisotope derivative label is selected from $^3$H, $^{11}$C, and $^{14}$C.

18. The method of claim 13 wherein the contacting step comprises direct application of the agent to a surgical site.

19. The method of claim 13 wherein the agent is dissolved or suspended in a solution suitable for surgical irrigation.

20. The method of claim 13 wherein the contacting step comprise a parenteral administration of the agent.

21. The method of claim 20 wherein the parenteral administration comprises subcutaneous injection, intraperitoneal injection, intramuscular injection, intravenous injection, intrathecal injection, intracerebroventricular injection, or intraspinal injection, or any combination thereof.

22. The method of claim 20 wherein the agent is dissolved or suspended in a solution suitable parenteral administration.

23. The method of claim 13 wherein the detecting step comprises:
applying a light source, tuned to the spectral excitation characteristics of the compound of Formula I, to the surgical field; and observing the surgical field through an optical filter tuned to the spectral emission characteristics of the compound of Formula I.

24. The method of claim 13 wherein the detecting step involves gamma imaging of the surgical site.

25. The method of claim 24 wherein the gamma imaging is PET, SPECT or both.

26. A method of imaging annulus fibrosus tissue comprising the steps of:
    administration of a radioisotope derivative of Formula I; and

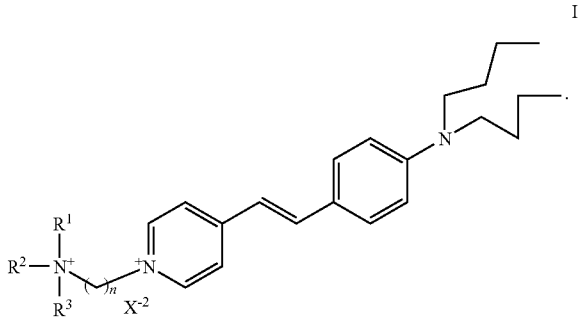

wherein $R^1$, $R^2$, and $R^3$ are each independently hydrogen, alkyl, substituted alkyl, fluroroalkyl, or perfluoroalkyl, n is an integer from two to four, and X is a counter ion forming a salt; and
    detecting the radioisotope derivative of Formula I by selectively imaging annulus fribrosus tissue within the spinal canal and intervertebral foramen.

27. The method of claim 26 wherein $R^1$, $R^2$, and $R^3$ are equal to $CH_3$, n is three, and X is Br.

28. The method of claim 26 wherein the administration comprises intrathecal injection, intracerebral injection, intracerebroventricular injection, or intraspinal injection, or any combination thereof.

29. The method of claim 26, wherein the radioisotope derivative label is selected from $^3H$, $^{11}C$, $^{14}C$, $^{18}F$, $^{32}P$, $^{35}S$, $^{123}I$, $^{125}I$, $^{131}I$, $^{36}Cl$, and $^{75}Se$.

30. The method of claim 29, wherein the radioisotope derivative contains a radioisotope label selected from $^3H$, $^{11}C$, $^{14}C$ and $^{18}F$.

31. The method of claim 26 wherein the detecting step involves gamma imaging.

32. The method of claim 31 wherein the gamma imaging is nuclear scintigraphy, PET, SPECT, or a combination thereof.

* * * * *